(12) United States Patent
Barry et al.

(10) Patent No.: US 10,352,906 B2
(45) Date of Patent: Jul. 16, 2019

(54) THROUGH-TRANSMISSION ULTRASONIC TESTING APPARATUS

(71) Applicant: Bell Helicopter Textron Inc., Fort Worth, TX (US)

(72) Inventors: Robert J. Barry, Arlington, TX (US); Edward A. Hohman, Mansfield, TX (US)

(73) Assignee: Bell Helicopter Textron Inc., Fort Worth, TX (US)

( * ) Notice: Subject to any disclaimer, the term of this patent is extended or adjusted under 35 U.S.C. 154(b) by 230 days.

(21) Appl. No.: 15/381,021

(22) Filed: Dec. 15, 2016

(65) Prior Publication Data

US 2018/0172642 A1    Jun. 21, 2018

(51) Int. Cl.
    *G01N 29/24*    (2006.01)
    *G01N 29/22*    (2006.01)
    *G01N 29/04*    (2006.01)

(52) U.S. Cl.
    CPC ......... *G01N 29/226* (2013.01); *G01N 29/043* (2013.01); *G01N 2291/023* (2013.01); *G01N 2291/0289* (2013.01); *G01N 2291/105* (2013.01); *G01N 2291/2694* (2013.01)

(58) Field of Classification Search
    CPC ............ G01N 2291/102; G01N 29/26; G01N 29/226; G01N 29/04; G01N 2291/023; G01N 2291/0289; G01N 2291/10
    USPC .................................................. 73/624, 632
    See application file for complete search history.

(56) References Cited

U.S. PATENT DOCUMENTS

| | | | | |
|---|---|---|---|---|
| 2,715,279 A | * | 8/1955 | Stromberg | G01B 5/08 200/61.42 |
| 3,190,111 A | * | 6/1965 | Trussell | G01N 29/04 248/219.1 |
| 4,574,615 A | * | 3/1986 | Bower | G01L 11/04 73/24.01 |
| 6,296,378 B1 | | 10/2001 | Doyen | |
| 6,484,583 B1 | | 11/2002 | Chennell et al. | |
| 6,681,632 B2 | * | 1/2004 | Chatellier | G01N 29/07 73/579 |
| 6,735,575 B1 | | 5/2004 | Kara | |
| 7,484,413 B2 | * | 2/2009 | Georgeson | G01N 29/07 73/624 |
| 7,614,304 B2 | | 11/2009 | Gunasekaran et al. | |
| 8,004,689 B2 | | 8/2011 | Monchalin et al. | |

(Continued)

FOREIGN PATENT DOCUMENTS

GB    2021280 A    11/1979
WO    2007005687 A1    1/2007

*Primary Examiner* — Helen C Kwok
*Assistant Examiner* — Nashmiya S Fayyaz
(74) *Attorney, Agent, or Firm* — Timmer Law Group, PLLC

(57) ABSTRACT

A testing apparatus, inspection system, and method for through-transmission ultrasonic testing. The testing apparatus includes a yoke having a support member with a pair of hinge joints, each hinge joint located on an end of the support member; a pair of arms extending from the support member having a hinge end and a pivotable transducer end, each arm being coupled to the hinge joint at the hinge end and extending to the pivotable transducer end; a pair of transducer support members disposed on each of the pivotal transducer ends; and a tension member connected to the pair of arms for aligning the pair of transducer support members during testing.

19 Claims, 12 Drawing Sheets

(56) References Cited

U.S. PATENT DOCUMENTS

2002/0017140 A1* 2/2002 Georgeson .......... G01N 29/225
  73/618
2012/0286094 A1 11/2012 Petsche et al.
2016/0061779 A1 3/2016 Barry et al.
2018/0184887 A1* 7/2018 Abou El Kheir ...... A61B 1/051

* cited by examiner

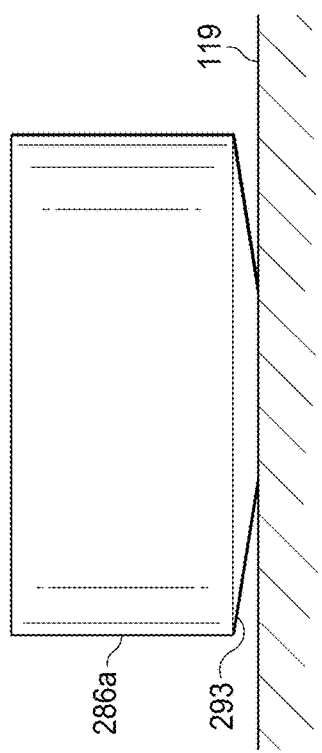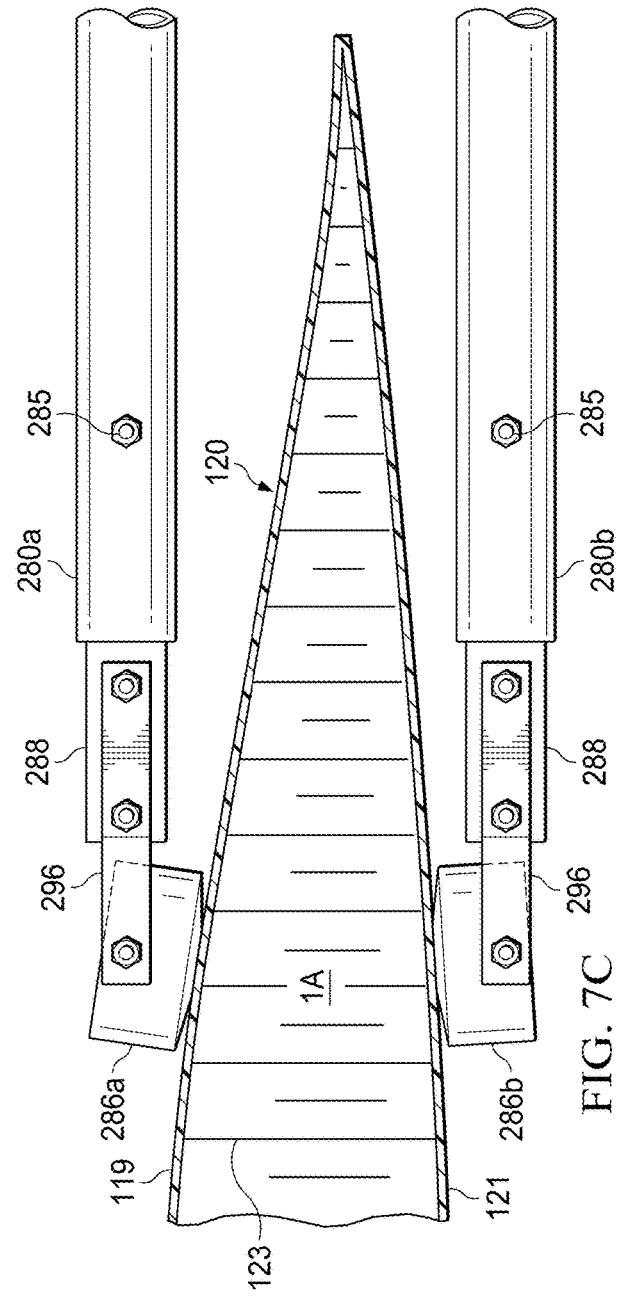

THROUGH-TRANSMISSION ULTRASONIC TESTING APPARATUS

BACKGROUND

Technical Field

The present disclosure relates to the ultrasonic inspection of parts, e.g. internally reinforced components for an aircraft.

Description of Related Art

In many industries, components are inspected for defects in a field environment. Non-destructive inspection of internally reinforced components often begins with tap testing or pitch-catch bond testing to identify any voids or disbond between an outer surface and the core. However, minor core damage on core-stiffened structures may provide a similar signal response to non-damaged core, which may cause a possible acceptable condition to be rejected. Through-transmission ultrasonic testing can quantify the attenuation difference between an adjacent good area and a suspect area to differentiate minor core damage from a disbond, thereby preventing an un-necessary repair.

An existing method of through-transmission ultrasonic testing involves "peaking" a signal by aligning two transducers located on opposite sides of the component being tested. Each transducer is moved by hand during this contact testing process. Additionally, the receiver amplification must be adjusted, while each transducer is held firmly in place. The hand-held technique is recommended for some manufacturing and field inspection procedures. However, it is not feasible to perform hand-held ultrasonic through-transmission on large areas of aircraft components, because ultrasonic transducer alignment is often too difficult.

There is a need for an apparatus that can improve through-transmission ultrasonic testing by assisting with the alignment of transducers.

SUMMARY

In a first aspect, there is provided a testing apparatus for through-transmission ultrasonic testing, including a yoke having a support member with a pair of hinge joints, each hinge joint located on an end of the support member; a pair of arms extending from the support member having a hinge end and a pivotable transducer end, each arm being coupled to the hinge joint at the hinge end and extending to the pivotable transducer end; a pair of transducer support members disposed on each of the pivotal transducer ends; and a tension member connected to the pair of arms for aligning the pair of transducer support members during testing.

In an exemplary embodiment, the pair of hinge joints imparts pivotal rotation of the pair of arms.

In an embodiment, each arm further includes a telescoping member to extend and retract the length of the arm.

In one embodiment, the pivotable transducer end can include a first pivot member for imparting rotation around a longitudinal axis of the arm.

In yet another embodiment, the pivotable transducer end can include a second pivot member for imparting rotation of the transducer support members around an axis perpendicular to a longitudinal axis of the arm.

In another embodiment, the tension member uniformly aligns the pair of arms.

In an embodiment, the tension member is a spring.

In one embodiment, the tension member is disposed adjacent to the support member.

In yet another embodiment, the tension member is generally parallel to the support member.

In an embodiment, the tension member is connected to the hinge end of the pair of arms.

In one embodiment, the tension member is a pair of input arms extending from the support member to the pair of arms.

In another embodiment, the input arms are pivotable at the support member and at the pair of arms.

In still another embodiment, the tension member is configured to impart uniform movement of the pair of arms.

In an embodiment, the pair of transducer support members is a first transducer support member and a second transducer member.

In one embodiment, each of the transducer support members has a beveled edge.

In a second aspect, there is provided a method to inspect a component, the method includes providing the testing apparatus, configuring an inspection system by positioning a first transducer in the first transducer support member and positioning a second transducer in the second transducer support member, providing a component having a first surface, a core, and a second surface; and positioning the inspection system so the first transducer support member is adjacent to the first surface and the second transducer support member is adjacent to the second surface. The first transducer is aligned with the second transducer within the respective support members.

In an embodiment, the step of positioning the inspection system includes pivoting the pair of arms at the pair of hinge joints.

In one embodiment, the step of positioning the inspection system includes rotating the pivotable transducer ends around a longitudinal axis of the arms.

In another embodiment, the step of positioning the inspection system includes rotating the first transducer support member around an axis perpendicular to the longitudinal axis of the arms.

In yet another embodiment, the step of positioning the inspection system includes rotating the second transducer support member around an axis perpendicular to the longitudinal axis of the arms.

In still another embodiment, the step of positioning the inspection system imparts uniform movement to the pair of arms.

In one embodiment, the method further includes telescopically extending the pair of arms.

Other aspects, features, and advantages will become apparent from the following detailed description when taken in conjunction with the accompanying drawings, which are a part of this disclosure and which illustrate, by way of example, principles of the inventions disclosed.

DESCRIPTION OF THE DRAWINGS

The novel features believed characteristic of the embodiments of the present disclosure are set forth in the appended claims. However, the embodiments themselves, as well as a preferred mode of use, and further objectives and advantages thereof, will best be understood by reference to the following detailed description when read in conjunction with the accompanying drawings, wherein:

FIG. 7B is a side view of a transducer support member, according to one example embodiment;

FIG. 7C is a side view of the transducer ends of the testing apparatus on a component, according to an example embodiment;

DESCRIPTION OF THE PREFERRED EMBODIMENT

Illustrative embodiments of the apparatus and method are described below. In the interest of clarity, all features of an actual implementation may not be described in this specification. It will of course be appreciated that in the development of any such actual embodiment, numerous implementation-specific decisions must be made to achieve the developer's specific goals, such as compliance with system-related and business-related constraints, which will vary from one implementation to another. Moreover, it will be appreciated that such a development effort might be complex and time-consuming but would nevertheless be a routine undertaking for those of ordinary skill in the art having the benefit of this disclosure.

In the specification, reference may be made to the spatial relationships between various components and to the spatial orientation of various aspects of components as the devices are depicted in the attached drawings. However, as will be recognized by those skilled in the art after a complete reading of the present application, the devices, members, apparatuses, etc. described herein may be positioned in any desired orientation. Thus, the use of terms such as "above," "below," "upper," "lower," or other like terms to describe a spatial relationship between various components or to describe the spatial orientation of aspects of such components should be understood to describe a relative relationship between the components or a spatial orientation of aspects of such components, respectively, as the device described herein may be oriented in any desired direction.

Figure 1:
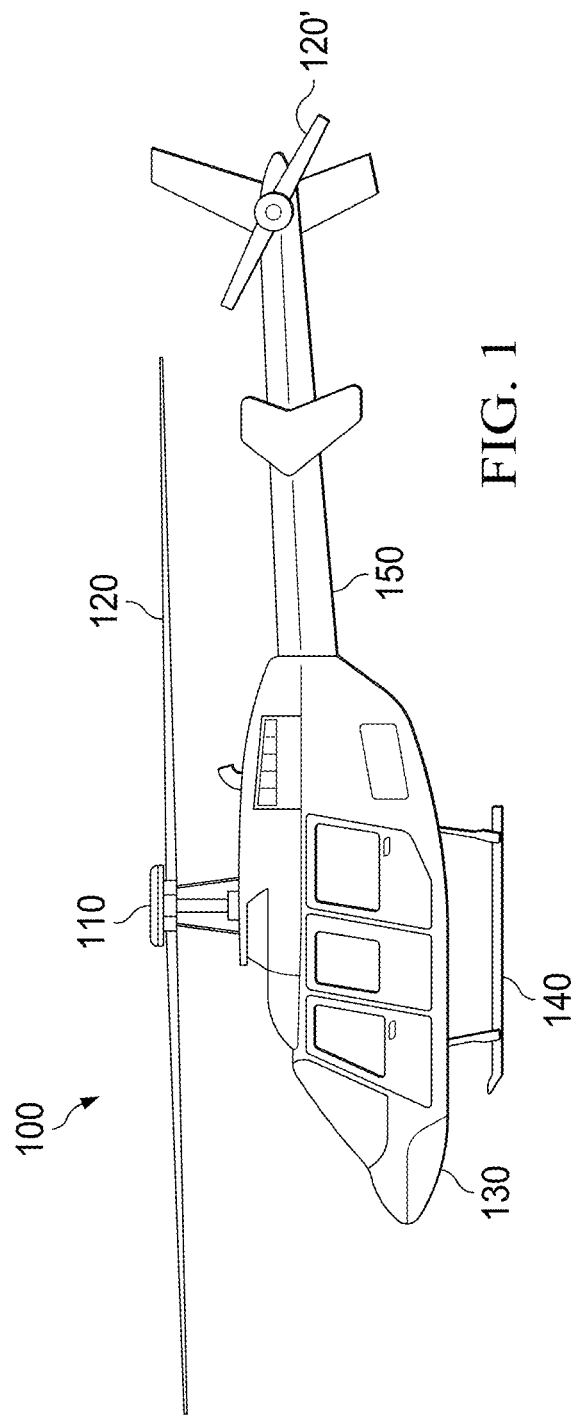
FIG. 1 is a perspective view of an aircraft, according to one example embodiment.

Referring to FIG. 1, a rotorcraft 100 is illustrated. Rotorcraft 100 includes a rotor system 110, a plurality of rotor blades 120, fuselage 130, a landing gear 140, and a tail member 150. It should be appreciated that rotorcraft 100 is merely illustrative of a variety of aircraft that can implement the apparatuses and methods disclosed herein.

Further, the apparatus and methods disclosed herein can be implemented to inspect and test components for a variety of aircraft structural implementations, for example, and not of limitation, propeller blade; rotor blades; structural members; flight controls, such as, rudders, ailerons, flaps, elevators, and spoilers; and wings. Even further the apparatus and methods disclosed herein can be implemented to inspect and test components in non-aircraft implementations, for example, and not limitation, space, watercraft, wind power, automotive, underwater, vehicle, and sporting components.

Figure 2:
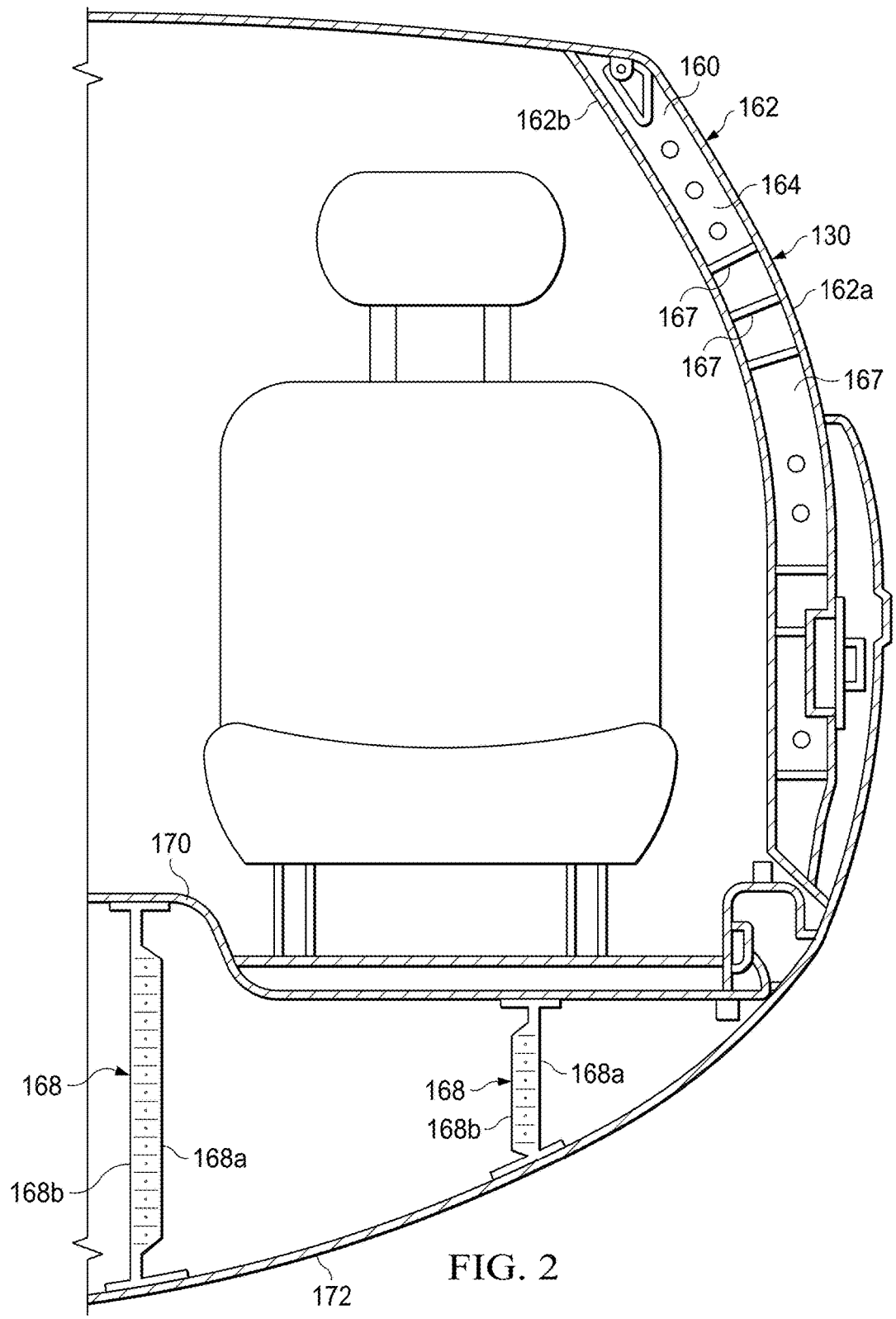
FIG. 2 is a side view of a fuselage side body, according to one example embodiment.

The fuselage 130 includes a side body 160. FIG. 2 illustrates the side body 160 has a first side wall 162 including an exterior wall 162a, a core 164, and an interior wall 162b. The core 164 includes core internal structures 167 that contribute to the aerodynamic and structural functionality of the fuselage 130. The core internal structures 167 can include multiple layers of materials sandwiched together; for example, but not limited to, carbon epoxy sheets and fiberglass sheets. The layers within the structure can have varied thicknesses. The core internal structures 167 can also include bracing members.

FIG. 2 also illustrates structural members 168 such as sub-floor structural members beneath removable floor panels 170. The structural members 168 may be configured in a longitudinal or transverse manner connecting the floor 170 to the outer fuselage structure 172. Fuel bladders and other hardware such as avionics and hydraulics are often located in the area between the floor panels 170 and outer fuselage structure 172 leaving limited space for testing of the structural members 168 using conventional hand-held methods and equipment. Some structural members 168 require removal for testing using conventional hand-held methods and equipment.

The core internal structures 167 and structural members 168 shown in FIG. 2 are not apparent from the exterior and may be beyond the arm-span reach of the inspector. In one embodiment, a method for identifying and inspecting core internal structures 167 and internal structural members 168 can be performed using a testing apparatus 250. The testing apparatus 250 can be used in an extended mode by extending arms 280 so that the testing apparatus 250 can reach an expanded testing area, which in some embodiments is beyond the arm-span reach of the inspector. In one contemplated embodiment, the outer diameter of the arms 280 is smaller than the outer diameter of an inspector's arm so the arms 280 of the testing apparatus 250 can reach and be positioned into confined spaces. The small outer diameter of the arms 280 advantageously permits positioning of the testing apparatus onto each of the structural members 168 without requiring the removal of hardware and disassembly that may be needed by conventional hand-held methods. For example, the arms 280 are positioned in extended mode sufficient to contact the sides 168a and 168b of the structural member 168 and have a small outer diameter to permit testing in a confined space without requiring removal of existing hardware such as the fuel bladders from the expanded testing area.

Figure 3:
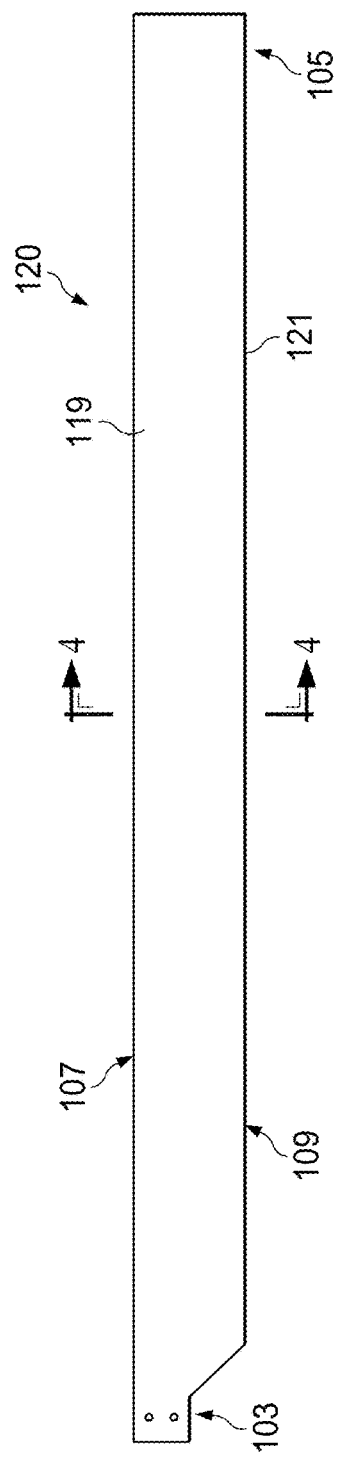
FIG. 3 is a top view of a rotor blade, according to one example embodiment.
Figure 4:
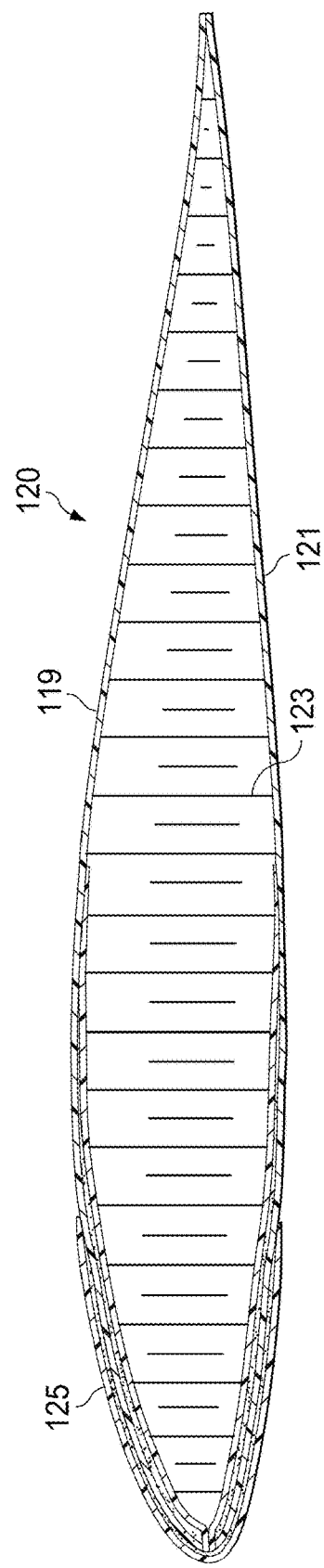
FIG. 4 is cross-sectional view of the rotor blade taken from section line 3-3 in FIG. 3, according to one example embodiment.

Referring now to FIGS. 3 and 4, an exemplary rotor blade 120 is illustrated. Rotor blade 120 has a root end 103 and a tip end 105, which define a span-wise axis therebetween. Rotor blade 120 also has a leading edge 107 and a trailing edge 109, which define a chordwise axis therebetween. It should be appreciated that rotor blade 120 is illustrative only and that alternative embodiments of rotor blade 120 can be configured in a variety of shapes and sizes. The rotor blade 120 can include a certain amount of built in twist for example a 10 to 12 degrees twist.

The rotor blade 120 can include a first surface 119, a second surface 121, core member 123, and an abrasion strip 125. The first surface 119 and second surface 121 can be an assembly of composite layers that are assembled and cured on one or more tools. The first surface 119 and the second surface 121 can have varying thicknesses and material layups which are implementation specific.

The core member 123 is illustrated herein as hex-shaped honeycomb core; however, the disclosure herein is not limited to hex-shaped core, rather other core shapes having variable core structures can also be implemented. The core member 123 can be uniquely tailored to have the local and global properties requisite to withstand the loading experienced by rotor blade 120 during operation. The internal variable core structures of the core member 123 are not readily apparent from the exterior, as shown in FIGS. 1 and 3.

Figure 5:
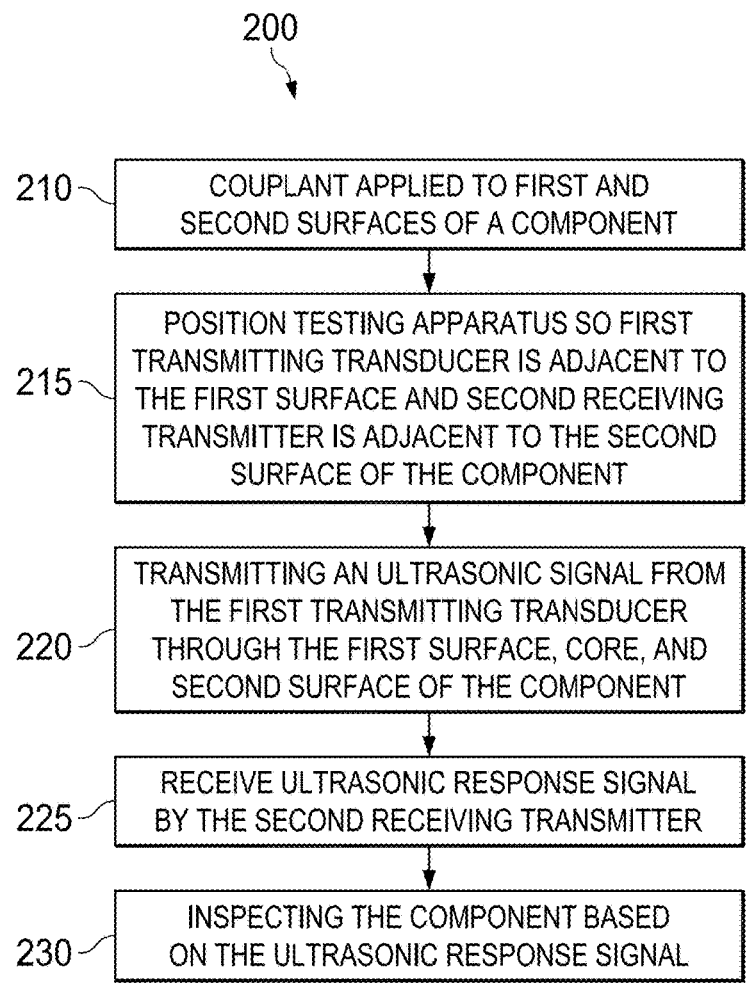
FIG. 5 shows a flowchart of an example inspection process for inspecting a component, according to one example embodiment.

A method for identifying and inspecting the internal structures of a component 200 is shown in FIG. 5 and refers to the rotor blade in FIGS. 3-4. A couplant or other lubricating system is applied on the first and second surfaces 210 to induce sound waves in the component being tested. The testing apparatus 250 is positioned by the operator so the first transmitting transducer 252 is adjacent to the first surface 119, and a second receiving transducer 254 is adjacent to the second surface 121 in step 215. The testing apparatus 250 can be positioned on the component using only one of the operator's hands, which leaves the second hand of the operator free to run and adjust the inspection system during the testing. For example, the operator can adjust the gain/receiver amplification with one hand while moving and positioning the testing apparatus on the component with the other hand. The step of positioning 215 can include twisting the testing apparatus 250 by the operator up or down to pivotably move a pair of arms disposed at hinge joints in the testing apparatus.

The step of positioning 215 of the testing apparatus can include telescopically extending a pair of arms in the testing apparatus 250 to extend the length of the testing apparatus for larger or curved components. The positioning step 215 can include rotating portions in each of the arms. A pivotable transducer end can be rotated around a longitudinal axis of the respective arm. A first and second transducer support members can rotate independently from each other and each can rotate around an axis perpendicular to the longitudinal axis of the respective arm. In one embodiment, the step of positioning 215 imparts uniform movement to the pair of arms.

During testing of the component, the transmitting transducer 252 sends an ultrasound wave signal through a first surface 119, core 123, and a second surface 121 in step 220. The receiving transducer 254 receives the ultrasonic signal response, which is the amount of sound that has reached the second surface 121 adjacent to the receiving transducer 254, in step 225. Imperfections or other conditions in the space between the transmitting transducer 252 and the receiving transducer 254 reduce the amount of sound transmitted, revealing their presence during the inspecting step 230.

FIGS. 6A-8 show one embodiment of the testing apparatus 250 for through-transmission ultrasonic testing. The testing apparatus 250 includes a yoke 260, a tension member 270, and a pair of arms 280. The testing apparatus 250 advantageously can hold the transducers 252 and 254 in alignment so the position of the transducers 252 and 254 are aligned and consistent during the positioning step 215 of the inspection process 200. The tension member 270 adjusts the positioning of the pair of arms 280 during step 215 without any engagement or disengagement operations by the operator.

The yoke 260 includes a support member 262 having a pair of hinge joints 264 located on a first end 262a and a second end 262b and a handle 268. During positioning, the operator can pivot the yoke 260 by the handle 268 to peak the signal between the transducers 252 and 254. The yoke 268 is constructed of lightweight components such as at least one of the following: aluminum, composite materials, extrusion material, or pultrusion materials.

The handle 268 is oriented generally parallel to the support member 262 and can include an ergonomic and comfortable grip to minimize hand fatigue by the operator. The handle 268 is fixedly connected to the support member 262 via a mounting assembly 267. In one embodiment, the mounting assembly 267 is a rail end type of clamp connected at flange 269a in parallel to the support member 262 on one end. The flange 269a has at least two holes for receiving two bolts, screws, or other conventional fasteners for securing the mounting assembly 267 to the support member 262. The opposite end of the mounting assembly 267 is fixedly connected to the handle 268 at flanges 269b and 269c. Each of the flanges 269b and 269c has holes for receiving bolts, screws, or other conventional fasteners.

The support member 262 serves as a spreader bar between the pair of arms 280 and can be tubular, square, or rectangular in shape. The support member 262 can be constructed of a lightweight extrusion or pultrusion material. In one embodiment, the support member 262 is from about 4 inches to about 11 inches in length. In another embodiment, the support member 262 is from about 7 inches to about 10 inches in length.

A pair of hinge joints 264 are located on the first and second ends 262a and 262b of the support member 262. The pair of hinge joints 264 includes a first and second channel portion 263a and 263b that provide openings for receiving an end of each of the arms 280. First and second pins 265a and 265b are each coupled to the support member 262 within a pair of diametrically opposed holes 266a and 266b, respectively. The first and second pins 265a and 265b can be a bolt, screw, or other conventional fastener sufficient to secure the pair of arms in the channel portions 263a and 263b. In an embodiment, bushing can be included with the first and second pins 265a and 265b.

In an embodiment, the hinge joint at the first end 262a of the support member 262 is in a locked position such that first arm 280a is oriented at a fixed 90 degree angle relative to the support member 262 during the positioning step 215. A locking bolt can be secured to the first pin 265a such that it secures the first arm 280a in the locked position for testing. The hinge joint at the second end 262b pivotally moves the second arm 280b upwards toward the first arm 280a. In an alternate embodiment, the hinge joint at the second end 262b is locked and the hinge joint at the first end 262a is movable.

The tension member 270 is operatively connected to the pair of arms 280 for positioning of the arms during the inspection process 215. The tension member 270 provides a light pressure to the transducers 252 and 254 so they remain adjacent to the first and second surfaces 119 and 121 during the inspection of the component. The tension member 270 can be oriented generally parallel to the support member 262 and secured within a fastener 271a and 271b in each of the arms 280. In one embodiment, the tension member 270 is attached to the pair of arms 280 at the hinge end 282. In another embodiment, the tension member 270 is attached to the pair of the arms 280 adjacent to pair of hinge joints 264. The tension member 270 is activated when the component is positioned between the first arm 280a and the second arm 280b.

An embodiment provides that the tension member 270 moves the first arm 280a towards the second arm 280b during the inspection process 200. In one embodiment, the tension member 270 moves the second arm 280b during the inspection process 200. Another embodiment includes moving both the first arm 280a and the second arm 280a using the tension member 270 to maintain alignment of the transducers 252 and 254.

In one embodiment, the tension member 270 is a spring. The spring is in its original form when the testing apparatus 250 is not in use or when the thickness of the component being tested is less than the gap between the transducer support members 286a and 286b. The spring is extended and thus activated from its original form when the thickness of the component being tested is more than the gap between the transducer support members 286a and 286b.

The pair of arms 280 includes the first arm 280a and the second arm 280b, which are constructed of lightweight, rigid material. The arms 280 must be stiff enough to remain laterally aligned when the arms 280 are moved in a span-wise and chord-wise motion during the step 215. In an embodiment, each of the arms 280a, 280b has an outer diameter of about 0.5 inches to about 1.5 inches. In one embodiment, each of the arms 280a, 280b has an outer diameter of about 0.7 inches.

Each arm includes a hinge end 282 that extends to a pivotal transducer end 284, which is opposite from the hinge end 282. In one embodiment, the total length of each arm 280 is about 28 to about 32 inches long. In another embodiment, the total length of the arm 280 is about 30 inches long. In yet another embodiment, the length of an arm 280a or 280b is from about two to about three times the length of the support member 262.

The pair of hinge ends 282 includes a pair of diametrically opposed holes for respectively receiving the pin 265a and 265b therein. Each arm rotates from the pin 265a around a hinge axis 261. The first arm 280a can rotate downward toward the second arm 280b. In one embodiment, the first arm 280a can rotate from about zero degrees to about −40 degrees relative to a hinge axis 261. The second arm 280b can rotate upward toward the second arm 280a. In an embodiment, the second arm 280b can rotate from about zero degrees to about 40 degrees relative to the hinge axis 261.

The first and second arms 280a and 280b are substantially symmetric; therefore, for the sake of efficiency the arms will be disclosed only with regard to the first arm 280a. However, one of ordinary skill in the art would fully appreciate an understanding of the second arm 280b based upon the disclosure herein of the first arm 280a.

The pivotal transducer end 284 is pivotally coupled to the hinge end 282. The pivotal transducer end 284 includes a transducer support member 286a for receiving a transducer 252. The pivotal transducer end 284 swivels respectively around the longitudinal and lateral axis of the first arm 280a as well as perpendicular to the first arm 280a to keep the transducer 252 flat on the changing geometry of the component during the positioning step 215.

Figure 6A:
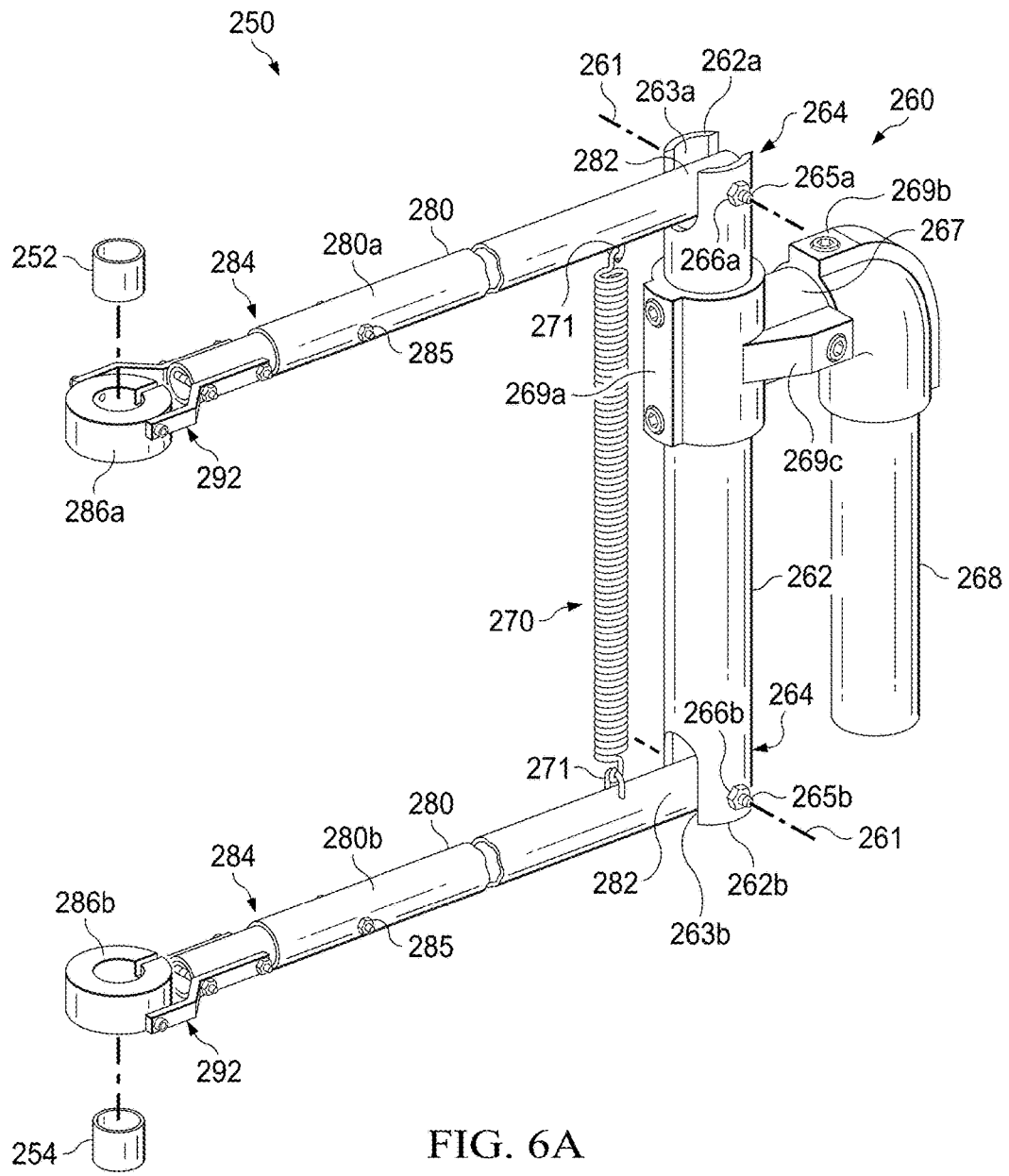
FIG. 6A is a perspective view of a testing apparatus, according to an example embodiment.
Figure 6B:
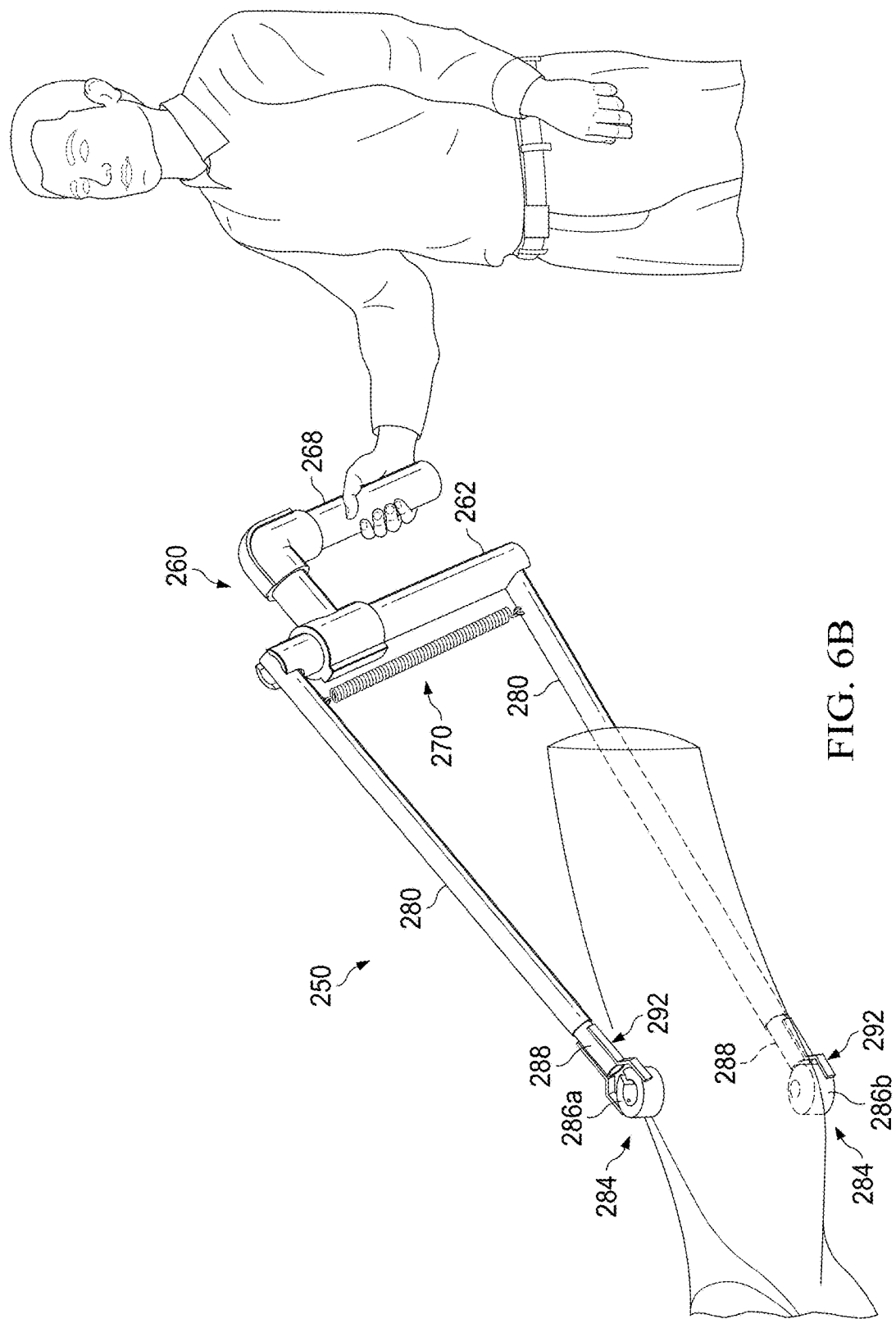
FIG. 6B is a perspective view of the testing apparatus in FIG. 6A tilted downward by the operator for testing a curved portion of a propeller rotor blade, according to one example embodiment.

The pivoting and rotating portions in the pivotal transducer end 284 combined with the hinge joints 264 permits the testing apparatus 250 to accommodate components having various twists, configurations, and angles as shown in FIG. 6B. The operator can move the testing apparatus 250 by tilting the handle 268 with one hand to change the chord contact position of the transducer support members 286a and 286b forward or aft. In one embodiment, the operator tilts the handle 268 forward and backward while keeping one of the transducer support members 286a and 286b in contact with the component, which causes the other transducer support member to be in contact with an opposite side of the component and to be aligned therewith sufficient for testing.

Figure 7A:
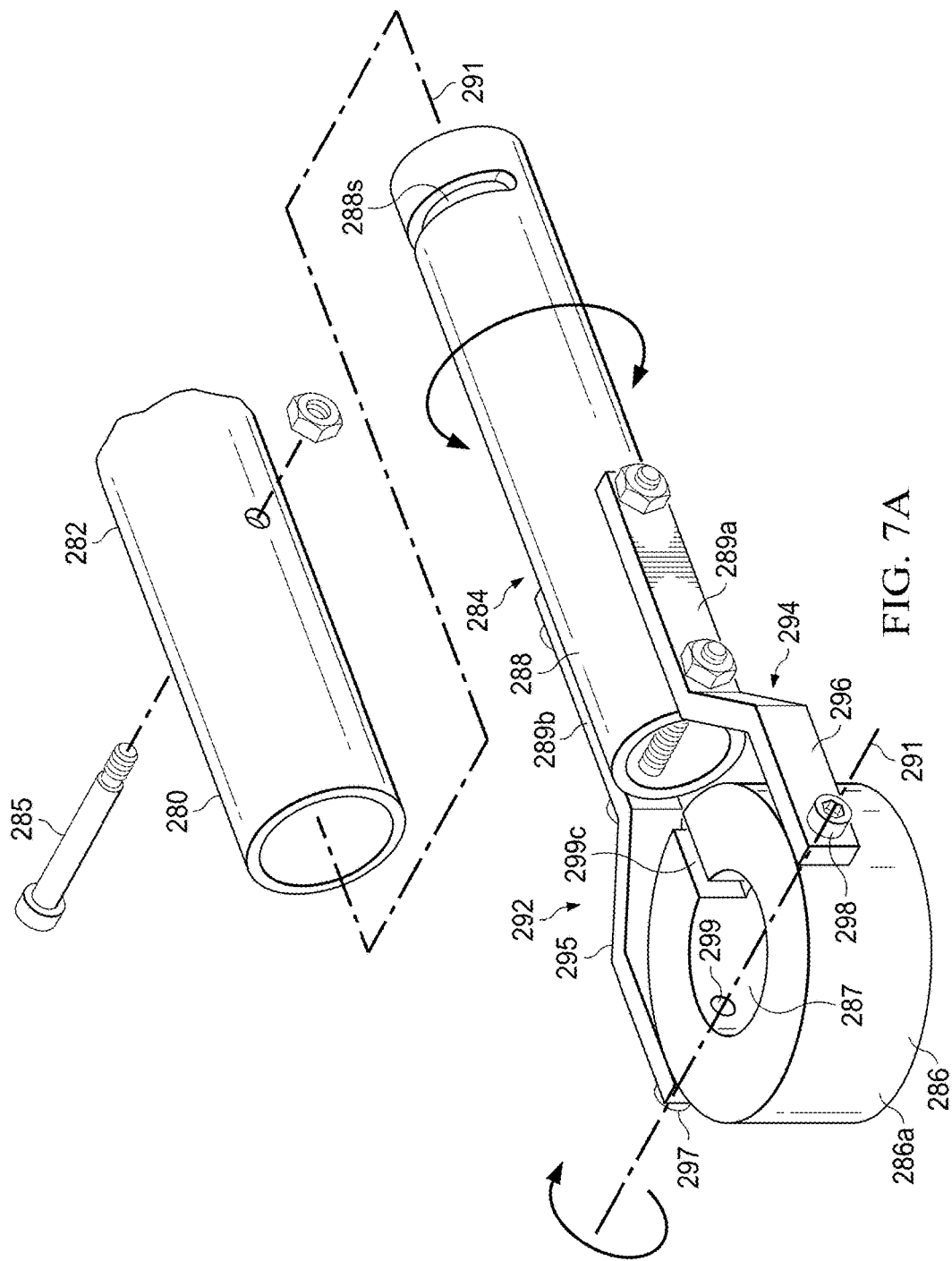
FIG. 7A is a perspective view of the transducer end of the testing apparatus, according to one example embodiment.

As shown in FIG. 7A, the pivotal transducer end 284 includes a first pivot member 288 and a second pivot member 292. The first pivot member 288 is located within the end of the arm 280a and is pivotably secured therein by a pair of slots 288s that receives bolt 285. The bolt 285 retains and controls the radial twist of the first pivot member 288. The first pivot member 288 rotates or is otherwise pivotable about a pivot axis 291 to facilitate the positioning of the transducer 252 during the positioning step 215. In one embodiment, the first pivot member 288 rotates about 50 degrees in a direction around the longitudinal axis 291 of the arm 280a.

The second pivot member 292 extends from the first pivot member 288 and provides a rotatable mount for the transducer support members 286a and 286b. The second pivot member is fixedly connected to the first pivot member 288 via flanges 289a and 289b having holes for receiving fasteners such as screws or bolts. The second pivot member 292 includes a yoke member 294 that has two support arms 295 and 296 each respectively having a hole therein for receiving pins 297 and 298. The yoke member 294 is disposed adjacent to an outer surface of the transducer support member 286. The pins 297 and 298 are positioned through the hole through a pair of diametrically opposed passages 299 in the transducer support member 286. The second pivot member 292 permits rotation of the support member 286a about an axis 291 that sufficient to maintain contact with a surface in the inspection area IA during the positioning step 215.

In one embodiment, the width of the second pivot member 292 along the axis 291 is from about 1.0 inches to about 3.0 inches. In an embodiment, the width of the second pivot member 292 along the axis 291 is less than 2 inches. In an embodiment, arm 280a has an outer diameter of about 0.7 inches and the transducer support member 286 has an off-set therefrom of about 0.3 inches to assist with clearance of the arm into confined locations during the positioning step.

The transducer support member 286a includes a central opening for receiving a transducer therein. The transducer 252 can be press fit into the central opening 287. In an embodiment, the transducer 252 is secured therein with a set-screw or other suitable fastener. As shown in FIG. 7B, the transducer support member 286a includes a beveled surface 293 circumferentially around the bottom of the transducer support member 286. The beveled surface 293 around the perimeter of the transducer support member 286 allows the transducer 252 to stay acoustically coupled to the component surface by gliding on the couplant as opposed to scraping off the couplant.

Figure 8:
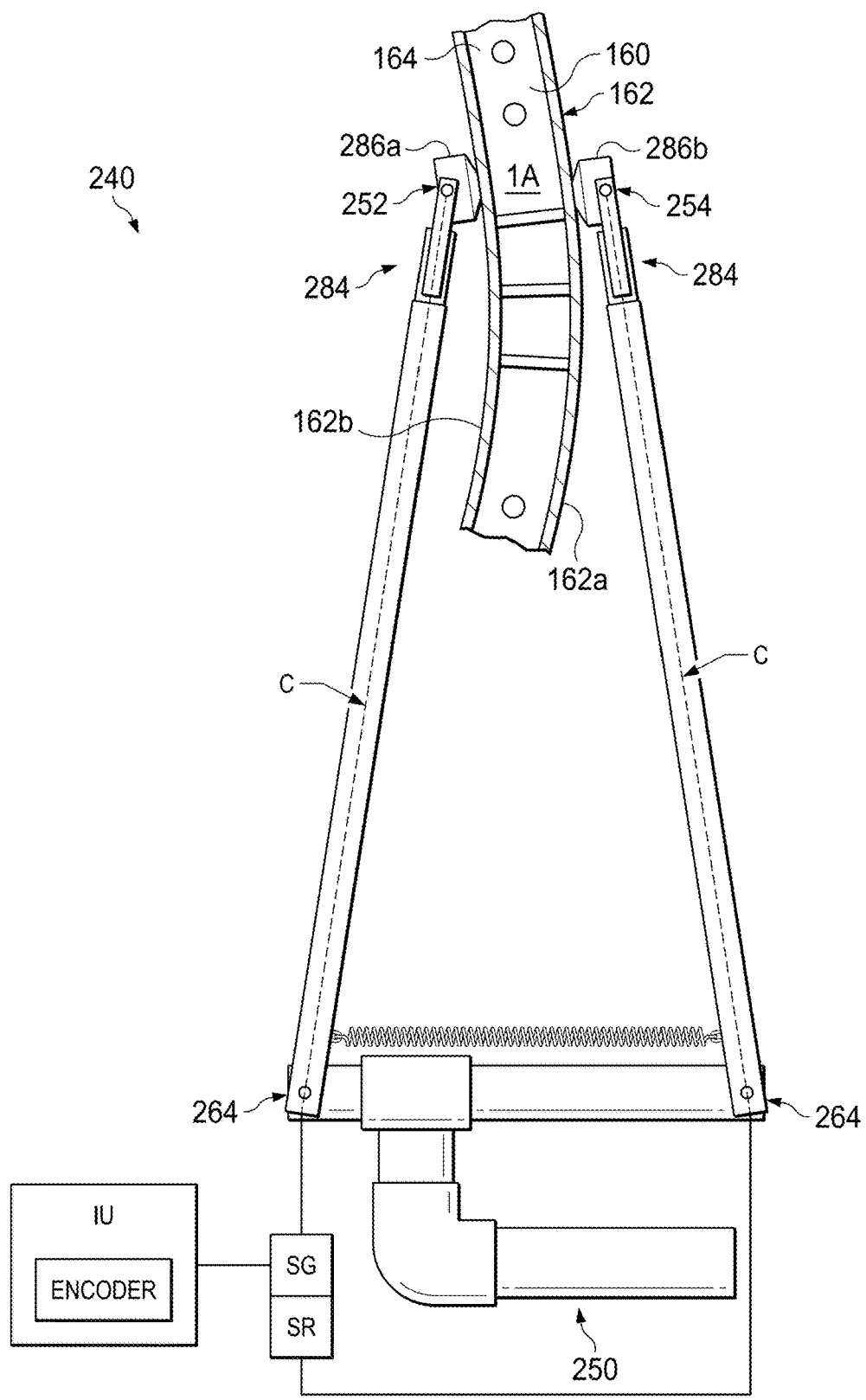
FIG. 8 is a schematic view of an inspection system including a testing apparatus inspecting a core section of the fuselage in FIG. 2, according to an example embodiment.

As shown in FIG. 8, the cable C for the transducer 252 can be received in a channel 299c in the transducer support member 286a and positioned within the arm 280a to prevent snagging of the cables during testing. Optionally the cable C for the transducer 252 can be positioned within the support member 262 so as to exit the second end 262b.

The first transmitting transducer 252 is a device that sends ultrasonic energy into the component. The second receiving transducer 254 is a device that receives ultrasonic energy through the component being tested as used in through-transmission technique. The first transmitting transducer 252 and second receiving transducer 254 are each received in a transducer support member 286a and 286b, respectively, prior to an inspection process.

In one embodiment, the first and second transducers 252 and 254 can be piezo electric transducers or other type of transducer. The first and second transducers 252 and 254 are piezo electric transducers having a frequency of at least 0.1 MHz to about 10 MHz. In other embodiments, the second transducer 254 receives ultrasonic energy in a pulse-echo technique. In this manner, the first and second transducers 252 and 254 can be used to detect defects within the component being tested. In some embodiments, the first and second transducers 252 and 254 are rigid or flexible transducer elements. In one embodiment, the first and second transducers 252 and 254 are commercially available as ½ inch diameter 1 MHz transducers from Olympus as A103S-RM model U8104008.

The transducer support members 286a and 286b can be fashioned or the transducers 252 and 254 can be replaced with transducers having different sizes or frequencies as needed to test a particular component. An exemplary embodiment includes a transducer with a frequency of 2.25 MHz when the core of the component being tested is suspected to have thin skins and small core cell node sizes. In another exemplary embodiment, the transducer has a frequency of 0.5 MHz when the core of the component being tested is suspected to have thicker skins and larger core cell sizes. In one embodiment, the transducers 252 and 254 are a testing device that benefits from being in contact with opposite sides of the surface of a component.

FIG. 8 is an illustration of the testing apparatus 250 as part of an inspection system 240 for inspecting a component. In this example, the component is a section of the fuselage 160 in FIG. 2. The inspection system includes the first transmitting transducer 252 and second receiving transducer 254 mounted on the support members 286a and 286b of the testing apparatus 250. The testing apparatus is held by the operator to position the first transmitting transducer 252 in an inspection area IA on the exterior surface 162a and the second receiving transducer 254 on the interior surface 162b of the fuselage side body 160.

The first transmitting transducer 252 is coupled to a signal generator SG, which transmits an ultrasonic signal to the transducer 252. For example, the ultrasonic signal can be an analog signal, a digital signal, an amplified signal, an electronic signal, or other type of signal. The signal generator SG can split a single ultrasonic signal into multiple ultrasonic signal portions to the transmitting transducer 252. In some embodiments, the signal generator SG generates an electronic pulse at a specific pulse repetition frequency, and the transmitting transducer 252 passes the ultrasonic signal into the exterior surface 162a of the first side wall 162 as an acoustic signal.

In one embodiment, the signal generator SG is a pulser that generates short, large amplitude electronic pulses of controlled energy, which are converted into short ultrasonic pulses by the transmitting transducer 252.

The transmitting transducer 252 passes the ultrasonic signal into the exterior surface 162a of the first side wall 162. The signal passes through the exterior surface 162a through the core internal structures 167 and then through the interior surface 162b to form a response signal representative of received ultrasonic pulses at the receiving transducer 254, which are received and amplified by the signal receiver SR.

The inspection system 240 includes an inspection unit IU that is connected to the signal generator SG and signal receiver SR. The inspection unit IU is used to inspect the fuselage side body 160 for defects based on the response signal. For example, the inspection unit IU can analyze the response signal from the receiving transducer 254 to determine if the received response signal indicates a defect in inspection area IA of the fuselage side body 160. After the inspection of inspection area IA, the testing apparatus 250 is repositioned to a different inspection area location, which can be on the same surface or a different surface on the fuselage side body 160.

The inspection unit IU can include an encoder that can detect the position of the transducers 252 and 254 on the surface of the fuselage side body 160. For example, the encoder can detect the position of the transducers 252 and 254 as the transducers are moved along the surfaces 162a and 162b of the fuselage side body 160.

In some embodiments, the inspection system records the response signal. In one embodiment, the data from the encoder can be included with the recorded response signals so that the data from the encoder can be used to identify the size and location of defects or features detected on the fuselage side body 160. By identifying defect locations, further analysis of the defects can be performed. Recording of the response signal can allow the inspections of multiple components or sections of the fuselage side body 160 to be compared. As such, manufacturing procedures, material compositions, etc. can be compared and improved based on the recorded signals.

Figure 9A:
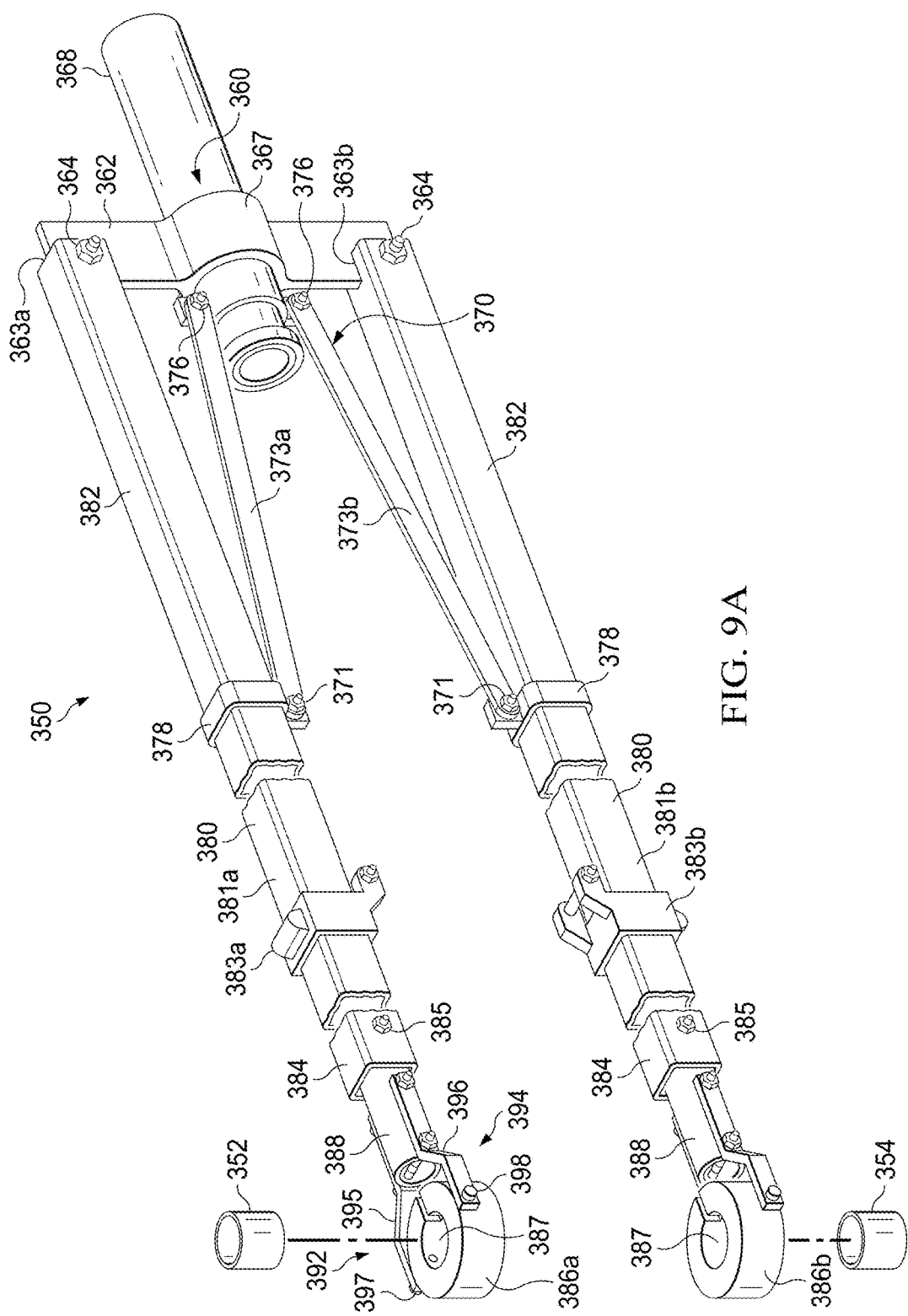
FIG. 9A is a perspective view of a testing apparatus, according to one example embodiment.
Figure 9B:
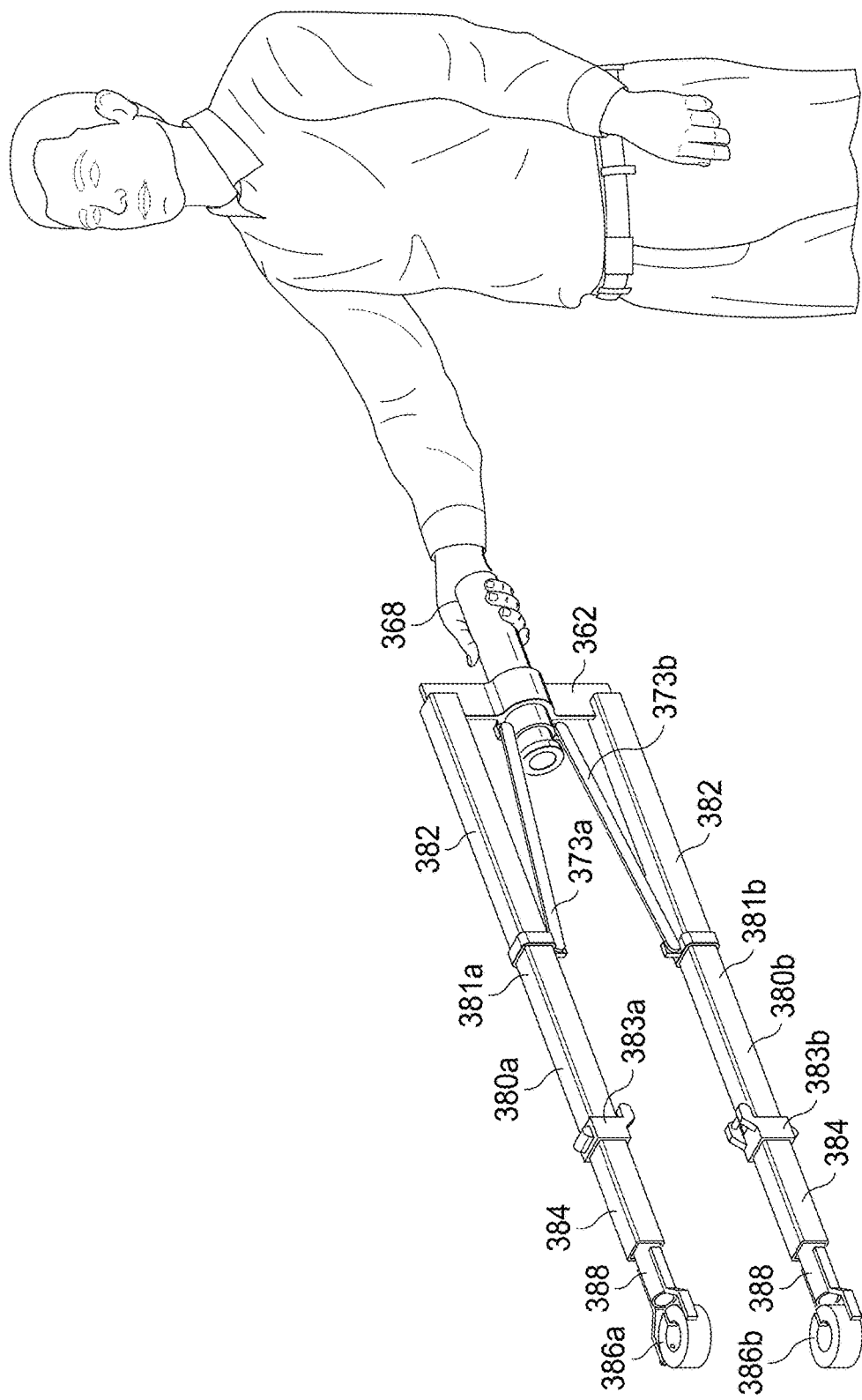
FIG. 9B is a perspective view of the testing apparatus in FIG. 9A with the telescoping members extended, according to one example embodiment.
Figure 10:
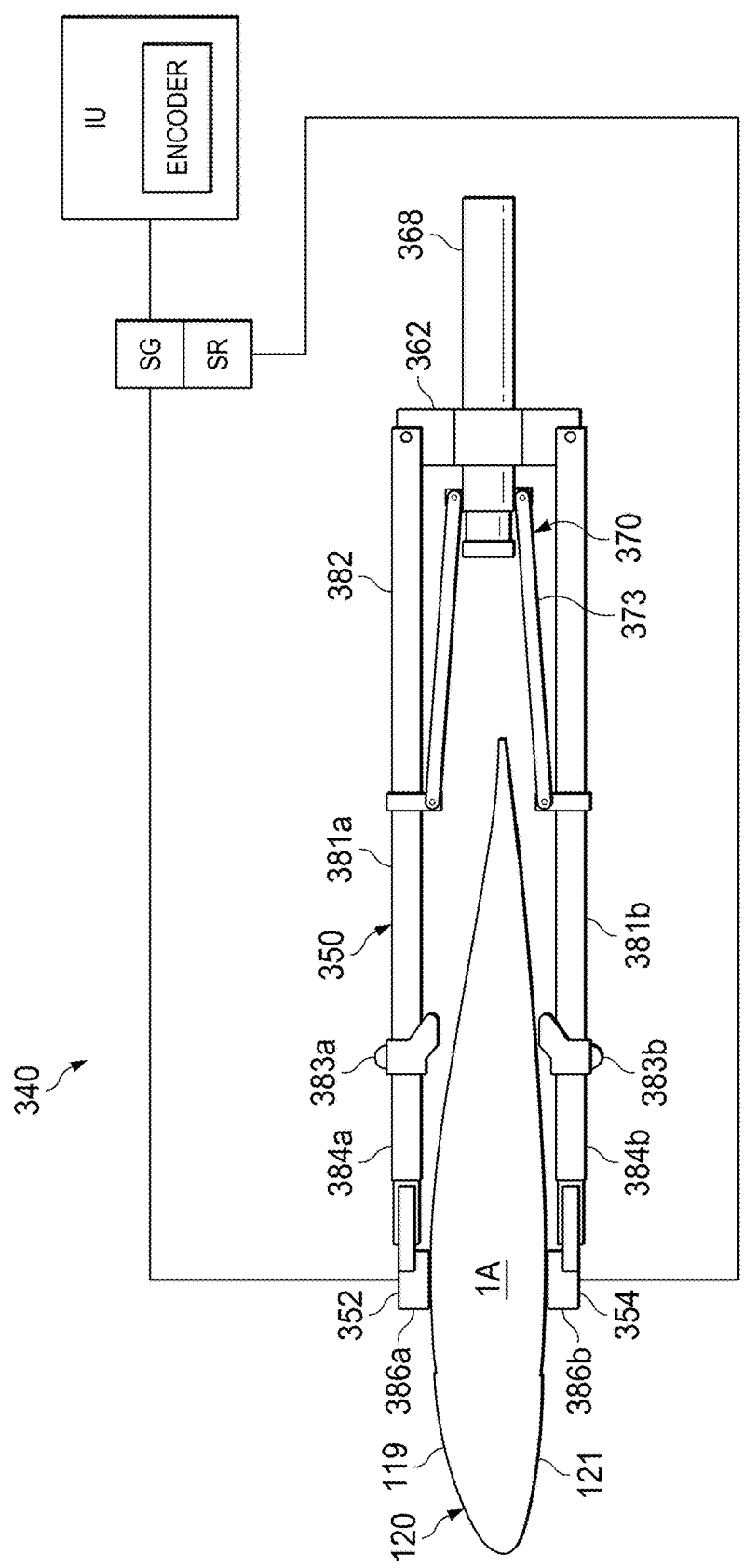
FIG. 10 is a schematic view of an inspection system including the testing apparatus shown in FIGS. 9A and 9B inspecting the rotor blade component in FIGS. 3-4, according to an example embodiment.

FIGS. 9A-10 are illustrative of an exemplary testing apparatus 250. Certain components of the testing apparatus are as described above in connection with the inspection system 240 and testing apparatus 250. Those components bear similar reference characters to the inspection system 240 and testing apparatus 250, but with a leading '3' rather than a leading '2'. The support member 362 in the testing apparatus 350 includes an integral mounting assembly 367 having an aperture. The yoke 360 further includes a handle 368 oriented generally perpendicular to the support member 362 and secured in mounting assembly 367. The handle 368 is secured by a set screw in the mounting assembly 367.

Each of the pair of arms 380 includes channels 363a and 363b for mating with the pair of hinge joints 364 on ends of the support member 362.

The testing apparatus 350 includes a tension member 370 that includes two input arms 373 extending from a support member 362. Each of the input arms 373 are symmetrical and includes a first pivot end 371 adjacent to the respective arm 380 and a second pivot end 376 adjacent to the support member 362. The first pivot end 371 is attached to a slidable member 378 that slides on arm 380 back toward the support member 362 as the first and second pivot ends 371 and 376 are pivoted outward. Each of the input arms 373 can include a torsion spring therein connected at one end to the arm 380a or 380b and at the other end to the support member 362 to assist positioning of the arms 380 toward each other. In one embodiment, the torsion spring is a 270 degree torsion spring. The tension member 370 in connection with the mounting assembly 367 ensures that the pair of arms 380 move uniformly and in the same amount when expanded or contracted by the operator.

In an embodiment, the second pivoting ends 376 are moved by the handle 368, e.g., the handle 368 is pushed inward through the mounting assembly 367 to cause the pivot ends 376 to pivot outward and expand the arms 380 outward. The handle 368 can be pushed outward through the mounting assembly 367 to pivot the pair of arms 380 together. The mounting assembly 367 can include lubrication, bearings or other friction relieving member to assist the operator in moving the handle through the mounting assembly 367.

As shown in FIG. 9B, the pair of arms 380 further includes a pair of telescoping members 381 to telescopically extend and retract the length of the pair of arms 380. Each of the telescoping members 381a and 381b can extend the length of the arm to about 5 feet and in a retracted position to about 2 feet. The telescoping members 381a and 381b are constructed of a lightweight, rigid material similar or identical to that of the pair of arms 380. The telescoping members 381a and 381b are slidably moved along arms 380a and 380b, respectively, and secured in position by locking members 383a and 383b. In one embodiment, each of the locking members 383a and 383b includes a hole for receiving a pin in tension by a spring disposed in a surface of the arm 380a or 380b. In an embodiment, a surface of the arms 380a and 380b includes a plurality of pins along the length of the arm to adjust the length of the arm. In one embodiment, the telescoping members 381a and 381b are each separately slidable.

FIG. 10 is an illustration of the testing apparatus 350 as part of an inspection system 240 for inspecting a component. In this example, the component is the rotor blade 120. The pair of telescoping members 381 are extended for positioning the transmitting transducer 352 on the first surface 119 and the receiving transducer 354 on the second surface 121.

The illustrative embodiments of the through-transmission ultrasonic testing apparatus include at least one of the following advantages: ultrasonic inspection of components with damage or suspected damage can be done faster and in a more repeatable manner; inspection of components can be achieved whether a component is on or off the aircraft; and by using the testing apparatus the ultrasonic through-transmission attenuation can be quantified by one person, e.g., the second hand of the operator can adjust the signal generator/signal receiver, no third hand is needed to hold the transducers on each side of the blade. In one embodiment, the testing apparatus and system provides the ability to inspect the core area of a rotor blade over thick doublers where pitch-catch inspection techniques are not as effective.

At least one embodiment is disclosed and variations, combinations, and/or modifications of the embodiment(s) and/or features of the embodiment(s) made by a person having ordinary skill in the art within the scope of the disclosure. Alternative embodiments that result from combining, integrating, and/or omitting features of the embodiment(s) are also within the scope of the disclosure. Where numerical ranges or limitations are expressly stated, such express ranges or limitations should be understood to include iterative ranges or limitations of like magnitude falling within the expressly stated ranges or limitations (e.g., from about 1 to about 10 includes 2, 3, 4, etc.; greater than 0.10 includes 0.11, 0.12, 0.13, etc.). For example, whenever a numerical range with a lower limit, $R_l$, and an upper, $R_u$, is disclosed, any number falling within the range is specifically disclosed. In particular, the following numbers within the range are specifically disclosed: $R=R_l+k*(R_u-R_l)$, wherein k is a variable ranging from 1 percent to 100 percent with a 1 percent increment, i.e., k is 1 percent, 2 percent, 3 percent, 4 percent, 5 percent, . . . , 50 percent, 51 percent, 52 percent, . . . , 95 percent, 96 percent, 97 percent, 98 percent, 99 percent, or 100 percent. Unless otherwise stated, the term "about" shall mean plus or minus 5 percent of the subsequent value. Moreover, any numerical range defined by two R numbers as defined in the above is also specifically disclosed. Use of the term "optionally" with respect to any element of a claim means that the element is required, or alternatively, the element is not required, both alternatives being within the scope of the claim. Use of broader terms such as comprises, includes, and having should be understood to provide support for narrow terms such as consisting of, consisting essentially of, and comprised substantially of. Accordingly, the scope of protection is not limited by the description set out above but is defined by the claims that follow, the scope including all equivalents of the subject matter of the claims. Each and every claim is incorporated as further disclosure into the specification and the claims are embodiment(s) of the present invention.

The invention claimed is:

1. A testing apparatus for through-transmission ultrasonic testing, comprising:
   a yoke having a handle and a support member with a pair of hinge joints, each hinge joint located on an end of the support member;
   a pair of extending arms extending from the support member, each extending arm having a hinge end and a pivotable transducer end, each extending arm being coupled to the hinge joint at the hinge end and extending to the pivotable transducer end, respectively;
   a pair of transducer support members disposed on each of the pivotal transducer ends; and
   a tension member comprises a pair of input arms extending from the support member to the pair of extending arms respectively, the tension member connected to the pair of extending arms for aligning the pair of transducer support members during testing.

2. The testing apparatus of claim 1, wherein the pair of hinge joints imparts pivotal rotation of the pair of extending arms.

3. The testing apparatus of claim 1, wherein each extending arm further comprises a telescoping member to extend and retract the length of the respective extending arm.

4. The testing apparatus of claim 1, wherein one of the pivotable transducer ends further comprises a first pivot member for imparting rotation around a longitudinal axis of the respective extending arm.

5. The testing apparatus of claim 4, wherein the other of the pivotable transducer ends further comprises a second pivot member for imparting rotation of the transducer support members around an axis perpendicular to a longitudinal axis of the respective extending arm.

6. The testing apparatus of claim 1, wherein the tension member uniformly aligns the pair of extending arms.

7. The testing apparatus of claim 1, wherein the pair of input arms further comprises respective pivot ends disposed adjacent to the support member.

8. The testing apparatus of claim 1, wherein the pair of input arms further comprises respective pivot ends disposed adjacent to the respective extending arm.

9. The testing apparatus of claim 1, wherein the input arms are pivotable at the support member and at the pair of extending arms.

10. The testing apparatus of claim 1, wherein the tension member is configured to impart uniform movement of the pair of extending arms.

11. The testing apparatus of claim 1, wherein the pair of transducer support members is a first transducer support member and a second support transducer member.

12. The testing apparatus of claim 1, wherein each of the pair of transducer support members has a beveled edge.

13. A method to inspect a component, the method comprising:
provide the testing apparatus of claim 11;
configuring an inspection system by positioning a first transducer in the first transducer support member and positioning a second transducer in the second transducer support member;
providing a component having a first surface, a core, and a second surface; and
positioning the inspection system so the first transducer support member is adjacent to the first surface and the second transducer support member is adjacent to the second surface;
wherein the first transducer is aligned with the second transducer;
wherein, during the positioning step, an operator pivots the yoke by the handle to peak a signal between the first transducer and the second transducer.

14. The method of claim 13, wherein the step of positioning the inspection system further comprising pivoting the pair of extending arms at the pair of hinge joints.

15. The method of claim 13, wherein the step of positioning the inspection system further comprises rotating the pivotable transducer ends around a longitudinal axis of the extending arms.

16. The method of claim 13, wherein the step of positioning the inspection system further comprises rotating the first transducer support member around an axis perpendicular to the longitudinal axis of the respective extending arm.

17. The method of claim 13, wherein the step of positioning the inspection system further comprises rotating the second transducer support member around an axis perpendicular to the longitudinal axis of the respective extending arm.

18. The method of claim 13, wherein the step of positioning the inspection system imparts uniform movement to the pair of extending arms.

19. The method of claim 13, further comprising:
telescopically extending the pair of extending arms.

* * * * *